(12) United States Patent
Bernard et al.

(10) Patent No.: US 6,217,941 B1
(45) Date of Patent: Apr. 17, 2001

(54) ISOCYANATES MODIFIED FOR BEING PROVIDED WITH SURFACTANT PROPERTY, COMPOSITION CONTAINING SAME, RESULTING COATING

(75) Inventors: Jean-Marie Bernard, Mornant; Thierry Jeannette, Garches; Minow Nabavi, Paris, all of (FR)

(73) Assignee: Rhodia Chimie, Boulogne-Billancourt (FR)

( * ) Notice: Subject to any disclaimer, the term of this patent is extended or adjusted under 35 U.S.C. 154(b) by 0 days.

(21) Appl. No.: 09/380,111

(22) PCT Filed: Mar. 2, 1998

(86) PCT No.: PCT/FR98/00405

§ 371 Date: Nov. 12, 1998

§ 102(e) Date: Nov. 12, 1999

(87) PCT Pub. No.: WO98/38196

PCT Pub. Date: Sep. 3, 1998

(30) Foreign Application Priority Data

Feb. 28, 1997 (FR) .................................................. 97 02406

(51) Int. Cl.⁷ ...................................................... B05D 3/02
(52) U.S. Cl. ...................... 427/358; 427/384; 427/321; 528/72; 560/24; 560/115; 560/157
(58) Field of Search ..................................... 427/355, 356, 427/358, 384, 421; 528/72; 560/24, 115, 157

(56) References Cited

U.S. PATENT DOCUMENTS 3,764,577 * 10/1973 Burns et al. .

FOREIGN PATENT DOCUMENTS 9-302309 * 11/1997 (JP) .

OTHER PUBLICATIONS translation of FR 1278286, Oct. 1961.*

* cited by examiner

*Primary Examiner*—Erma Cameron
(74) *Attorney, Agent, or Firm*—Jean-Louis Seugnet

(57) ABSTRACT

The invention concerns a compound of formula (I)

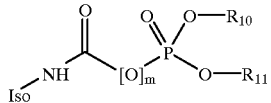

in which m is to 0 or 1 Iso is the (poly)isocyanate radical (after elimination of an isocyanate function); $R_{10}$ is selected among: a negative charge; a hydrocarbon-based radical (i.e. a residue containing hydrogen and carbon atoms) having a carbon as it binding point [i.e. the atom carrying the open bond ]; $R_{11}$ is selected among: a negative charge. The invention is applicable to organic synthesis.

23 Claims, No Drawings

ISOCYANATES MODIFIED FOR BEING PROVIDED WITH SURFACTANT PROPERTY, COMPOSITION CONTAINING SAME, RESULTING COATING

This application is an application under 35 U.S.C. Section 371 of International Application Number PCT/FR98/00405, filed on Mar. 2, 1998.

The present invention relates to a family of isocyanates which are modified to give them a surfactant property.

The present invention relates to isocyanate-based compounds and compositions (which can be partially masked, but this is not the preferred embodiment). The invention is also directed toward the process for using them, their use for making coatings and the coatings thus obtained. The invention relates more particularly to compositions which are (self)dispersible in aqueous phase.

In order to give a better understanding of the invention it has appeared appropriate to make the following reminders.

In the present description, the particle size characteristics often refer to notations of the type $d_n$ in which n is a number from 1 to 99. This notation is well known in many technical fields, but is slightly rarer in chemistry, and it may thus be useful to recall its meaning. This notation represents the particle size such that n% (by weight, or more exactly by mass, since weight is not an amount of matter but rather a force) of the particles is less than or equal to said size.

In the description hereinbelow, the polydispersity index will be used, which is defined as $$I=(d_{90}-d_{10})/d_{50}$$

In the paints and varnishes sector, diisocyanates are widely used, in particular alkylene diisocyanates (for example those sold under the brand Tolonate®) and derivatives thereof of biuret type or trimers thereof.

However, two problems remain incompletely solved to date, namely:
- the use of organic solvents, whose presence is reputed to be toxic and harmful to the environment;
- the need to provide on the market non-volatile products, which has led to the molecules being made heavier, by oligomerizing the diisocyanates; this solution is not entirely satisfactory since it uses an elaborate, and thus expensive, function to solve the problem.

Needless to say, these problems must be solved while at the same time satisfying the constraints intrinsic to coatings.

To make films of paints or of varnishes, a dispersion or an emulsion containing the isocyanate, which may be blocked, on the one hand, and a dispersion or a solution of polyol, on the other hand, are mixed together.

The mixture of the dispersions, which can also contain pigments, in particular titanium dioxide, the dispersion of which is improved by the present invention, and fillers, is then applied to a support in the form of a film with the aid of the standard techniques for using industrial paints. When the preparation contains blocked isocyanates, the film plus support assembly is cured at a temperature which is sufficient to release the isocyanate functions and to condense them with hydroxyl groups of the polyol particles. However, it should be recalled that masked or blocked products have a significantly higher cost price than non-masked products.

The use of organic solvents is increasingly being criticized by the authorities in charge of safety at work, since these solvents, or at least some of them, are reputed to be toxic or chronotoxic. For this reason, efforts are being made to develop more and more techniques which replace the solvent-medium techniques in order to overcome the drawbacks associated with solvents.

One of the solutions most frequently used lies in the use of emulsions or dispersions in water. On account of the reactivity of water with isocyanates, this solution is especially used for masked isocyanates.

In order not to end up between Scylla and Charybdis, a major stumbling block is to be avoided, namely the deterioration of one or more of the essential qualities of the coatings [smooth nature (to avoid the "orange-peel" appearance), hardness, resistance to solvents, etc.]; in particular, poor adhesion of the coating to its support should be feared. The reason for this is that many surfactants are reputed to impair the integrity of the link between the coating and its support and are known and used to undermine the attachment between a polymer and a support (cf., for example DE-OS 3,108,537).

When unmasked or incompletely masked isocyanates are used, their useable lifetime remains less than a few hours, in general one or two hours.

Thus, it is important not to encounter any difficulties during the emulsification or dispersion of the isocyanates.

Accordingly, one of the aims of the present invention is to provide a compound and a composition which, by mixing in water or, more specifically, in an aqueous phase, gives an emulsion without it being necessary therefor to use specific techniques and/or plants.

Another aim of the present invention is to provide a compound and a composition of the above type which does not disrupt the coating operations.

Another aim of the present invention is to provide a compound and a composition of the above type whose solvent content is less than ⅕, advantageously less than ⅒, on a mass basis relative to said composition. Needless to say, it is preferable for there to be as little solvent as possible, or even none at all.

These aims and others which will become apparent hereinbelow are achieved by means of compounds of formula (I) and of compositions, in which they comprise at least one compound of formula (I)

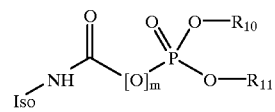

in which m is equal to zero or, advantageously, to 1;

in which Iso is a (poly)isocyanate residue (after removal of an isocyanate function);

in which $R_{10}$ is chosen from:
- a negative charge;
- a hydrocarbon-based residue (i.e. a residue containing hydrogen and carbon atoms) whose point of attachment [i.e. the atom bearing the open bond] is a carbon;

in which $R_{11}$ is chosen from:
- a negative charge;

a group of formula II:

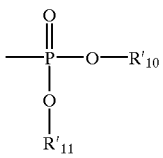

in which $R'_{10}$ is chosen from hydrocarbon-based residues (similar to or different from $R_{10}$) and a negative charge whose point of attachment [i.e. the atom bearing the open bond] is a carbon in which $R'_{11}$ is (are) chosen from hydrocarbon-based residues whose point of attachment [i.e. the atom bearing the open bond] is a carbon (similar to or different from $R_{10}$ and $R'_{11}$) and a negative charge.

Although this does not form part of the preferred compounds, it should be noted that when the similar or different organic substituents ($R_{10}$; $R'_{11}$; $R'_{10}$) do not comprise a polyethylene glycol chain fragment, it is preferable for them to be $C_8$ to $C_{12}$ alkyl, advantageously branched, or a $C_{12}$ to $C_{16}$ aralkyl or a $C_{10}$ to $C_{14}$ alkylaryl.

It is desirable for at least one of the similar or different organic substituents ($R_{10}$; $R'_{11}$; $R'_{10}$) to contain a polyethylene glycol chain fragment advantageously of at least 5, preferably of at least 7, ethylene oxide units. In other words, it is desirable for at least one of the organic substituents to correspond to the same formula as the substituents of E in the general formula I. More specifically, at least one of the organic substituents ($R_{10}$; $R'_{11}$; $R'_{10}$) corresponds to the formula:

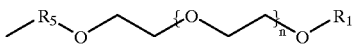

where $R_5$ represents an arm containing not more than two carbon-based chain members where n is an integer chosen between 0 and 30, advantageously between 5 and 25, preferably between 9 and 20 (closed intervals, i.e. including the limits);

where $R_1$ represents a hydrocarbon-based radical advantageously chosen from optionally substituted aryls and alkyls.

Said lipophilic part $R_1$ is generally chosen from alkyl groups [in the present description alk-yl is taken in its etymological sense as the hydrocarbon-based residue of an alkan-ol after ignoring the alcohol (or -ol) function]; and aryl groups. When the number of ethylene glycol functions is not more than 5, the simple alkyls are advantageously branched, advantageously $C_8$ to $C_{12}$, the aralkyls are $C_{12}$ to $C_{16}$, the alkylaryls are $C_{10}$ to $C_{14}$ and the simple aryls are $C_{10}$ to $C_{16}$. If not, the lipophilic part can vary widely, especially when the number of ethylene glycol units is greater than 10, and can thus constitute a hydrocarbon-based radical of at least 1, advantageously of at least 3, and containing not more than 25, advantageously not more than 20, carbon atoms.

It is advantageous for the Iso radical to afford, predominantly or totally, an aliphatic bond with the same preferences as those outlined above with regard to the isocyanates.

These compounds are derived from the decarboxylative condensation of isocyanate, which is advantageously aliphatic, with partially neutralized phosphoric acid and phosphates.

The compounds of formula:

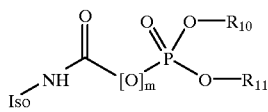

in which $R_{10}$ and $R_{11}$ can take the above values, but also, when m is 1, can be a negative charge on account of the fact that there may be significant amounts of residual phosphoric acid in certain batches, thus also form part of the invention.

Needless to say, $R_{10}$ can then also be equal to:

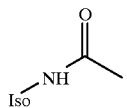

The Iso radical may or may not then be the same as that of the penultimate formula, in which Iso represents a polyisocyanate residue, advantageously the residue of a product of reaction of a diisocyanate monomer to form biuret or isocyanurates (trimer) or with a di- or polyol, advantageously a triol or a tetraol.

It is advantageous for the Iso radical to afford, predominantly or totally, an aliphatic bond with the same preferences as those outlined above with regard to the isocyanates.

In addition to the function featured in the formula, Iso advantageously bears at least one, and preferably at least two, isocyanate functions, preferably at least one of which is not masked and more preferably at least two of which are not masked.

However, according to a preferred embodiment of the present invention, it has been shown that it may be advantageous to replace most or even all of the isocyanate functions with those specified above. This gives a compound which is both stable and inert with respect to isocyanate compositions, which can be added to the isocyanate compositions without any specific precaution.

The preferred isocyanates for the complete reaction above are low-viscosity isocyanates, especially aliphatic isocyanates; mention may be made in particular of the simple monomer, preferably of polymethylene diisocyanate and advantageously hexamethylene diisocyanate, and derivatives of the "trimerization" reaction which gives di-, tri-, tetra-, penta-, hexa- or heptafunctional isocyanates, advantageously trifunctional isocyanates.

A subject of the present invention is also compositions comprising at least one compound of formula (I).

More specifically, they comprise, in particular:

a sub-composition which is a vector of isocyanate functions, the preferred characteristics of which will be specified later, and a surfactant containing at least one compound of formula (I);

optionally, an aqueous phase.

Thus, according to one advantageous variant of the present invention, the compositions according to the present invention comprise compounds derived from the reaction outlined above in an overall proportion, relative to a volume of one liter of isocyanate, of from 0.01 to 1, advantageously from 0.05 to 0.5 and preferably from 0.05 to 0.3, equivalent of function:

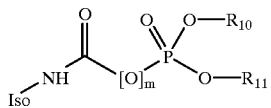

in which m is equal to zero or 1.

According to the present invention, said compound can be used alone or as a mixture with one or more surfactants. These surfactants can be agents also corresponding to formula (I).

These optional surfactants can also be chosen from other ionic compounds [in particular aryl and/or alkyl sulfate(s) or phosphate(s) (obviously, aryl in particular encompasses alkylaryls and alkyl in particular encompasses aralkyls), aryl or alkyl phosphonate, phosphinate or sulfonate, fatty acid salt and/or zwitterionic salt] and from nonionic compounds which may or may not be blocked at the end of the chain (however, the nonionic compounds containing alcohol functions on at least one of the chains appear to have a slightly unfavorable effect on the (self)emulsion, although they have a favorable effect on other aspects of the paint composition; taking all of this into account, it is preferable that the content of this type of compound should represent not more than one-third, advantageously not more than one-fifth, preferably not more than one-tenth, of the mass of said anionic compounds according to the invention).

The countercation is advantageously monovalent and is chosen from inorganic cations and organic cations that are advantageously non-nucleophilic and, consequently, of quaternary or tertiary nature (in particular oniums from column V, such as phosphonium, ammoniums, or even from column VI, such as sulfonium, etc.) and mixtures thereof, usually ammoniums, generally derived from an amine, advantageously a tertiary amine. Advantageously, an organic cation containing a hydrogen which is reactive with the isocyanate function is avoided. This results in a preference for tertiary amines.

The inorganic cations can be sequestered by phase-transfer agents such as crown ethers.

The pKa of the cations (organic [ammonium, etc.] or inorganic) is advantageously between 8 and 12.

The cations, and in particular the amines, corresponding to the ammoniums, advantageously have no surfactant property, but it is desirable that they should have good solubility, or in any case sufficient solubility to ensure that of said compounds of formula (I) anionic and advantageously a polyethylene glycol chain fragment, in aqueous phase and at the working concentration. Tertiary amines containing not more than 12 carbon atoms, advantageously not more than 10 carbon atoms, preferably not more than 8 carbon atoms, per "onium" function (it is reminded that there is preferably only one of these per molecule) are preferred. The amines can contain other functions, and in particular functions corresponding to amino acid functions and cyclic ether functions such as N-methylmorpholine, or otherwise. These other functions are advantageously in a form which does not react with the isocyanate functions and does not significantly impair the solubility in aqueous phase.

It is very desirable for the anionic compounds according to the present invention to be in a neutralized form, such that the pH induced during a dissolution or a placing in contact with water is at least equal to 3, advantageously to 4, preferably to 5, and not more than 12, advantageously not more than 11, preferably not more than 10.

The mass ratio between the surfactant compounds (including said compound of formula (I)) and the isocyanates is very preferably between 4 and about 10%; the recommended zones will be explained later.

The composition can also comprise a catalyst, advantageously a latent catalyst (which can be released by the action of external agents, for example visible or UV radiation, oxygen).

The isocyanate composition according to the invention can, after dispersion or emulsification in an aqueous phase, comprise a water content of from 10 to 70%. The emulsion is an oil-in-water emulsion.

However, in the course of the study which led to the present invention, in particular in the case of aliphatic isocyanates (i.e. isocyanates connected to the hydrocarbon-based skeleton (i.e. a skeleton containing both hydrogen and carbon) via a saturated ($sp^3$) carbon), it has been shown that there is a risk of various reactions getting out of control when certain proportions of water are reached. Thus, it is recommended to avoid compositions in which the mass ratio between the amount of water in the aqueous phase, on the one hand, and the sum of the isocyanate and the surfactant according to the invention, on the other hand, is between $10^{-2}$ and 0.5. If greater safety is desired, ratios between $10^{-3}$ and 1 will be avoided.

The emulsions obtained have, for the isocyanate part, $d_{50}$ values at least equal to 0.1 micrometer, usually 0.5 micrometer, and they have a $d_{50}$, preferably a $d_{80}$ advantageously less than or equal to (at most equal to) 5 micrometers, preferably 3 micrometers.

The aqueous phase of the emulsion generally serves as a vector for the co-reagents which are polycondensable with the isocyanate functions and, in this case, comprises compounds containing functions (advantageously not more than 4, preferably not more than 3 functions; cf. the explanation below for the polyols which general mutatis mutandis to all the functionality of this type) bearing reactive hydrogens, in general one or more polyols.

This polyol is a polymer which contains at least two hydroxyl groups (phenol or alcohol) advantageously having a hydroxyl content of between 0.5 and 5%, advantageously between 1 and 3% (by mass). With the exception of the latices which will be recalled below, it advantageously comprises not more than 4, and preferably not more than 3, primary alcohol functions (but usually two since the actual crosslinking [brought about by a functionality statistically greater than two (fractional value possible)] is generally generated by the polyisocyanates). However, it may also comprise secondary or tertiary alcohol functions (in general not more than about 10, advantageously not more than 5 and usually not more than two), which, in general, do not react or react only after the primary alcohol functions, and in the order: primary, secondary, tertiary.

Polyoses or polyosides (starch, cellulose, various gums (guar, carob, xanthan, etc.)), especially in solid form, are to be avoided. In the form of a texturing agent, and provided that this does not harm the emulsification or emulsion stability, they can, however, be used to give specific properties (for example thixotropic properties, etc.). The polymer skeleton can be of varied chemical nature, in particular acrylic, polyester, alkyd, polyurethane or even amide, including urea.

The polyol can comprise anionic groups, in particular carboxylic or sulfonic groups, or can comprise no ionic groups.

In the context of the present invention, it has been shown that the present of an anionic carboxylate function ($—CO_2—$) significantly increases the drying kinetics, which is particularly advantageous for obtaining rapid "dust-free"

drying, in particular when operating externally. A significant effect can be noted for a ratio of at least one carboxylic function to approximately 20 functions containing reactive hydrogen [alcohol or phenol function], advantageously for a ratio of one to about 10, preferably for a ratio of one to about 5; however, it is desirable for this ratio to be at most equal to one function to one function, preferably one carboxylic function to two ol functions. The carboxylate countercations advantageously satisfy the same preferences as those explained for the countercations in the compound according to the present invention.

The polyol can already be in aqueous or water-soluble or water-dispersible medium.

This can be an aqueous solution (which can be obtained in particular after neutralization of the ionic groups) or an emulsion of the polymer in water or a latex-type dispersion.

It appears to be possible to disperse a standard polyisocyanate in a water-soluble polyol under certain formulation conditions (in particular with a suitable ratio of pigment to paint binder). However, the use of standard polyisocyanates with water-dispersed polyols (such as resin or latex emulsions) often poses problems of incompatibility (flocculation, appearance of several phases, etc.). One of the many advantages of the preparation according to the invention is that it offers great freedom of choice for the formulation (physical form of the polyol, ratio of pigment to binder, ease of incorporation into aqueous media).

Moreover, it has been found through the typical values of coatings (in particular chemical resistance and hardness), that the crosslinking of the films is much greater when the polyol used is carboxylated.

In particular, it is advantageously possible to use latices, especially nanolatices (i.e. latices whose particle size is nanometric [more specifically whose $d_{50}$ value is at most equal to about 100 nanometers]).

Thus, according to one of the particularly advantageous embodiments of the present invention, the polyol is advantageously a nanometer-sized latex which has the following characteristics:

$d_{50}$ of between 15 and 60 nm, advantageously between 20 and 40 nm carboxylate function of 0.5 to 5% by mass -ol function: between 1 and 4%, advantageously between 2 and 3% solids content: between 25 and 40% a $d_{80}$ value of less than 1 micrometer.

In addition, especially when their glass transition temperature is less than 0° C., advantageously less than –10° C. and preferably less than –20° C., the latices allow high-quality resistance to bad weather and in particular to temperature variations to be obtained, even with aromatic isocyanates.

The molar ratio between the free isocyanate functions and the hydroxyl functions is between 0.5 and 2.5, advantageously between 0.8 and 1.6, advantageously between 1 and 1.4.

The latices (not functionalized with isocyanate, optionally masked) described in the French patent application filed on Apr. 28, 1995, No. 95/05123, and in the corresponding European patent application No. EP 0,739,961, give very good results.

Thus, advantageously, the latex particles have an accessible acid function (advantageously carboxylic acid function) content of between 0.2 and 1.2 milliequivalent/gram of solid material and they have an accessible alcohol function content of between 0.3 and 1.5 milliequivalent/gram.

Thus, as indicated in this document, the preferred latices are those consisting of particles bearing function(s) according to the invention, are hydrophobic and advantageously have a size ($d_{90}$) generally of between 0.01 micrometer and 10 micrometers and preferably not more than 5 micrometers, or even 2 micrometers. They are calibrated, monodisperse and present in the latex in a proportion ranging between 0.2 and 65% by weight relative to the total weight of the latex.

The weight-average molecular mass ($M_w$, preferably determined by gel permeation chromatography, known as "GPC") of the polymers constituting the particles of population A (latex containing an -ol function acting as polyol) is advantageously between $5 \times 10^4$ and $5 \times 10^6$, preferably $1.1 \times 10^5$ and $2 \times 10^6$.

The alcohol functions or the acid, preferably carboxylic acid, functions can also be obtained by hydrolysis of alcohol-generating functions (ester, ether, halide, etc.) or acid-generating functions (ester, anhydride, acid chloride, amide, nitrile, etc.).

The distribution between the various types of units advantageously satisfies the following rules:

The content of unit derived from the monomer consisting of said free alcohol containing an activated ethylenic function, and relative to the total amount of units of any kind, is advantageously between 3 and 15%, preferably between 4 and 10% (mole or equivalent).

According to one advantageous embodiment of the present invention, the unit is derived from an ester of an α-ethylenic acid with a diol, one of the alcohol functions of which remains non-esterified. Said diol is advantageously an ω/ω' diol, advantageously chosen from 1,4-butanediol, 1,3-propanediol and glycol.

It is desirable for said α-ethylenic acid to be an optionally substituted acrylic acid.

According to one preferred embodiment of the present invention, the content of unit derived from a free carboxylic acid (or in the form of one of its salts), and relative to the total amount of units of any kind, is between 2 and 10% (mole).

For economic reasons, it is often advantageous for said free acid to be an optionally monosubstituted acrylic acid or one of its salts.

The particles obtained from the present invention can consist of two separate polymers, the first constituting the core and the second constituting the periphery. This type of particle can be obtained by epipolymerization [in which a latex seed is coated by surface polymerization (epipolymerization, occasionally referred to as superpolymerization)] of a separate polymer. The core is occasionally known as the seed by analogy with the phenomenon of crystallization. In this case, only the second polymer, i.e. the surface polymer, satisfies the concentration constraints for the various functions according to the present invention.

These optional surfactants can also be chosen from other ionic compounds [in particular aryl and/or alkyl sulfate(s) or phosphate(s) (obviously, aryl in particular encompasses alkylaryls and alkyl in particular encompasses aralkyls), aryl or alkyl phosphonate, phosphinate or sulfonate, fatty acid salt and/or zwitterionic salt] and from nonionic compounds which may or may not be blocked at the end of the chain (however, the nonionic compounds containing alcohol functions on at least one of the chains appear to have a slightly unfavorable effect on the (self)emulsion, although they have a favorable effect on other aspects of the paint composition; taking all of this into account, it is preferable that the content of this type of compound should represent not more than one-third, advantageously not more than one-fifth, preferably not more than one-tenth, of the mass of said compounds of formula (I) according to the invention).

According to one particularly advantageous embodiment of the present invention, after dispersion or emulsification, the sum of the constituents in the binder (i.e. the mass contents of the isocyanate(s), emulsifier(s) and polyol(s)) in water ranges from 30 to 70% relative to the total amount of the composition.

The isocyanates targeted by the invention in particular comprise the compounds detailed below.

These compounds can advantageously contain the structures common in this field, for example prepolymers derived from the condensation of polyol (for example trimethylol propane), in general triol (which is advantageously primary, see later regarding the definition of the polyols) and especially the most common structures, i.e. those of isocyanurate type, also known as trimer, uretidine dione structures, also known as dimer, biuret or allophanate structures or a combination of structures of this type on a single molecule or as a mixture.

If it is desired to lower the solvent content of the composition substantially, in particular when it is in emulsion form, it is preferable to use mixtures of this type which naturally (i.e. without addition of solvent) have a low viscosity. The compounds with this property are especially the derivatives (such as isocyanurate, also known as trimer, uretidine dione structures, also known as dimer, biuret or allophanate structures or a combination of structures of this type on a single molecule or as a mixture), partial and/or total, of the aliphatic isocyanates whose isocyanate functions are connected to the skeleton via ethylene fragments (for example polymethylene diisocyanates, in particular hexamethylene diisocyanate and those arylenedialkylene diisocyanates whose isocyanate function is remote from the aromatic rings by at least two carbons, such as (OCN—[$CH_2$]$_t$—Φ—[$CH_2$]$_u$—NCO) with t and u greater than 1). These compounds or mixtures advantageously have a viscosity at most equal to about 3000 centipoises (or millipascal.seconds), preferably to about 1500 centipoises (or millipascal.seconds).

When these values are not reached, it is then often useful to bring the mixture to these viscosity values by adding a minimum amount of suitable solvent(s). As already mentioned above, the isocyanates concerned can be mono-, di- or even polyisocyanates. Advantageously, these derivatives can contain structures of isocyanurate type, also known as trimer, uretidine dione structures, also known as dimer, biuret or allophanate structures or a combination of structures of this type on a single molecule or as a mixture.

The isocyanate monomers can be:
aliphatic, including cycloaliphatic and arylaliphatic, such as:
  like simple aliphatic, polymethylene diisocyanates and in particular hexamethylene diisocyanate;
  like partially aliphatic "neopentyl" partially cyclic (cycloaliphatic) isophorone diisocyanate (IPDI);
  like cyclic aliphatic (cycloaliphatic) diisocyanate, those derived from norbornane;
  arylenedialkylene diisocyanates (such as OCN—$CH_2$—Φ—$CH_2$—NCO, a portion of which shows no essential difference from the aliphatics, i.e. those whose isocyanate function is remote from the aromatic rings by at least two carbons, such as (OCN—[$CH_2$]$_t$—Φ—[$CH_2$]$_u$—NCO) with t and u greater than 1;
or aromatics, such as tolylene diisocyanate.

The preferred polyisocyanates targeted by the technique of the invention are those in which at least one, advantageously two, preferably three, of the conditions below are satisfied:

at least one, advantageously at least two, of the NCO functions are connected to a hydrocarbon-based skeleton via a saturated (sp$^3$) carbon, preferably with at least one, preferably at least two, of the sub-conditions below:
  at least one, advantageously two, of said saturated (sp$^3$) carbons bears at least one, advantageously two, hydrogen(s), (in other words, it has been found that better results are obtained when the carbon bearing the isocyanate function bears a hydrogen, preferably two hydrogens);
at least one, advantageously two, of said saturated (sp$^3$) carbons are themselves borne by a carbon, which is advantageously aliphatic (i.e. of sp$^3$ hybridization), which itself bears at least one, advantageously two, hydrogen(s); in other words, it has been found that better results are obtained when the carbon bearing the isocyanate function is not in a so-called "neopentyl" position;
all the carbons via which the isocyanate functions are connected to the hydrocarbon-based skeleton are saturated (sp$^3$) carbons which advantageously partly, preferably totally, bear a hydrogen, preferably two hydrogens; in addition, it is advantageous for said saturated (sp$^3$) carbons themselves to be at least partially (advantageously one-third, preferably two-thirds), preferably totally, borne by a carbon, advantageously an aliphatic carbon (i.e. a carbon of sp$^3$ hybridization), which itself bears at least one, advantageously two, hydrogen(s); in other words, it has been found that better results are obtained when the carbon bearing the isocyanate function is not in a so-called "neopentyl" position;
particularly suitable polyisocyanates are those which contain, at least partially, an isocyanuric or biuret skeleton (whether this skeleton is derived from only one or from several monomers, see below) and more specifically structures such as isocyanurate, also known as trimer, uretidine dione structures, also known as dimer, biuret or allophanate structures or a combination of structures of this type on a single molecule or as a mixture.

When the polyisocyanates are relatively heavy, i.e. when they comprise at least 4 isocyanate functions, the first two conditions become:
at least one-third, advantageously two-thirds, of the NCO functions are connected to a hydrocarbon-based skeleton via a saturated (sp$^3$) carbon;
at least one-third, advantageously two-thirds, of said saturated (sp$^3$) carbons bears at least one, advantageously two, hydrogen(s), (in other words, it has been found that better results are obtained when the carbon bearing the isocyanate function bears a hydrogen, preferably two hydrogens); in addition, it is advantageous for said saturated (sp$^3$) carbons themselves to be at least partially (advantageously one-third, preferably two-thirds), preferably totally, borne by a carbon, advantageously an aliphatic carbon (i.e. a carbon of sp$^3$ hybridization), which itself bears at least one, advantageously two, hydrogen(s); in other words, it has been found that better results are obtained when the carbon bearing the isocyanate function is not in a so-called "neopentyl" position.

Another aim of the present invention is to provide a process of the above type which makes it possible to emulsify the composition targeted above when it contains no water.

This aim and others which will become apparent hereinbelow are achieved by means of an emulsification process which comprises at least the following step:
addition, advantageously with very moderate stirring, of the isocyanate(s) to the polyol+water mixture.

The surfactant can be either in the aqueous phase or, preferably, in the isocyanate phase. In the first case, the reactions between isocyanate and said compound comprising an anionic function and advantageously a polyethylene glycol chain fragment are much more limited.

This stirring is preferably manual or mechanical.

This emulsification is advantageously conducted at a temperature below 50° C., preferably at room temperature.

It is desirable, if necessary, to adjust the pH (to reach a value advantageously at least equal to three, preferably 4, and advantageously not more than 11, preferably 10, and thus advantageously between 3 and 11, preferably between 4 and 10) during the emulsification. This adjustment makes it possible to arrive at an advantageous zone in which the first (or only) acidity of each surfactant according to the present invention is neutralized.

According to one advantageous variant of the present invention, the pigments (and in particular the titanium dioxide) are dispersed in the polyol(s) before addition of the isocyanate.

Another aim of the present invention is to provide a process for applying the isocyanate-based composition to form a coating.

These aims and others which will become apparent hereinbelow are achieved by means of a process comprising the application of a preparative coat (i.e. a coat of composition according to the invention comprising the aqueous phase and the constituents of the coat) whose thickness before drying is between 10 and 400 micrometers, advantageously between 50 and 200 micrometers, corresponding, after drying, to a thickness of between 5 and 150 micrometers, advantageously between 20 and 80 micrometers.

According to one advantageous embodiment, this process comprises a drying operation from 20° C. to 60° C. for a period which can range from ¼ to 24 hours.

Advantageously, this drying operation takes place in the presence of a solvent to assist the removal of water.

According to one particularly advantageous embodiment of the present invention, the application is performed by spraying.

The preparation of the surfaces is well known to those skilled in the art (for example phosphatations for ferrous steel compounds or chromation for alumina-based surfaces) (reference may be made, for example, to the following books: "Organic Coating Technology" Volume II by H. F. Payne and "Paint Handbook" edited by G. E. Weismantel).

According to the present invention, it is thus possible to obtain coatings (in particular paints or varnishes) which have the following technical characteristics (these values depend especially on the polyols used):

| Implementation and characteristics of the coating Iso2178 dry thickness: 45 μm Support and treatment thereof: steel treated by phosphatation: R461 plates from the supplier Q Pannel | | |
|---|---|---|
| | Minimum properties obtained | Usual |
| DIN test 67530 (these values are only of interest when a gloss paint is desired, but not when a matt or satin paint is desired) | | |
| 20° gloss | 0.5 | 80 |
| 60° | 0.5 | 90 |
| Konig Iso 1522 hardness | 10s | 150s |

| Implementation and characteristics of the coating Iso2178 dry thickness: 45 μm Support and treatment thereof: steel treated by phosphatation: R461 plates from the supplier Q Pannel | | |
|---|---|---|
| | Minimum properties obtained | Usual |
| DIN 53151 adhesion test | GT-1 | GT-5 |
| Impact strength test No. Iso 6272 | | |
| direct | 10 cm | >100 cm |
| inverse | 5 cm | >100 cm |
| Resistance to methyl, ethyl ketone (butanone) (Passage twice) | 20 | >200 |
| External QUV content DIN 53384 | 50 h | 800 h |

The nonlimiting examples below illustrate the invention.

EXAMPLE 1

Synthesis of HDT isocyanate whose functions are totally converted into compound according to the invention (reference CMI 972).

114 g of Rhodafac RE 610 are loaded into a three-necked flask. 26.3 g of triethylamine are then added with stirring. The temperature of the reaction medium then rises from 21.8° C. to 39.6° C. 30 g of Tolonate HDT with an NCO titer equal to 0.521 are then added at 31.5° C. The temperature of the reaction medium rises to 37° C.

After reaction for 2 hours after addition of the Tolonate, the temperature of the reaction medium is 29.4° C. Infrared analysis on a sample indicates the presence of isocyanate functions. After reaction for three hours, infrared analysis of a sample indicates the presence of free isocyanate functions. 7 g of Rhodafac RE 610 mixture neutralized with triethylamine are then added in the same ratio as indicated above. After reaction for 4 h 40 min after addition of the Tolonate, infrared analysis of a sample indicates the absence of free isocyanate functions.

The product is then stored in a 250 ml flask and used in the tests of aqueous emulsification of polyisocyanates.

EXAMPLE 2

Emulsification of the reference product CMI 972 of composition such that:

RE 610 pre-neutralized with TEA

HDT/RE 610 ratio=1/1 molar (30 g of HDT+114 g of RE 610+26 g of TEA)

The 90/10 (by weight) HDT/CMI 972 mixture is self-emulsifiable (0.96 μm SYMPATEC).

The coatings obtained using this emulsion are of high quality.

What is claimed is:

1. A composition of matter comprising:
   (a) a sub-composition comprising isocyanate functions;
   (b) a surfactant containing a compound, having the following formula (I):

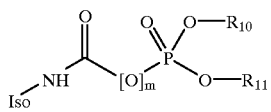

wherein:
   m is equal to 0 or 1;
   Iso is a (poly)isocyanate residue after removal of an isocyanate function;

$R_{10}$ is a negative charge or a residue containing hydrogen and carbon atoms whose point of attachment is a carbon atom; and $R_{11}$ is a negative charge or a grout of formula II:

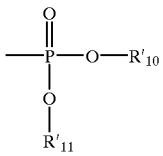

wherein $R'_{10}$ is a residue containing hydrogen and carbon atoms, or a negative charge whose point of attachment is a carbon and wherein $R'_{11}$ is a residue containing hydrogen and carbon atoms whose point of attachment is a carbon atom, or a negative charge; and, optionally, (c) an aqueous phase.

2. A composition according to claim 1, comprising, relative to a volume of one litre of isocyanate(s), a quantity of 0.01 to 1 equivalent of function of formula:

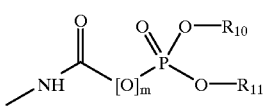

wherein:

m is equal to 0 or 1;

$R_{10}$ is a negative charge or a residue containing hydrogen and carbon atoms whose point of attachment is a carbon atom; and $R_{11}$ is a negative charge or a group of formula II:

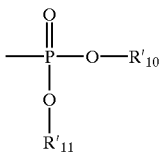

wherein $R'_{10}$ is a residue containing hydrogen and carbon atoms, or a negative charge whose point of attachment is a carbon and wherein $R'_{11}$ is a residue containing hydrogen and carbon atoms whose point of attachment is a carbon atom, or a negative charge.

3. A composition according to claim 2, comprising from 0.05 to 0.3 equivalent of function of formula:

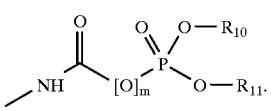

4. A composition according to claim 1, wherein said sub-composition (a) comprises, on a mass basis, at least 5%, of isocyanate function.

5. A composition according to claims 1, wherein said sub-composition (a) comprises, on a mass basis, not more than about 50%, of isocyanate function.

6. A composition according to claims 4, wherein said sub-composition comprises, on a mass basis, at least 15%, and not more than about 30%, of isocyanate function.

7. A composition according to claim 1, wherein said sub-composition (a) is formed from aliphatic isocyanates.

8. A process for making a coating, comprising the steps of:

(1) applying a coating of a composition as defined in claim 1.

9. A process according to claim 8, further comprising the step of:

(2) drying said coating at a temperature of 20° C. to 50° C. for ¼ to 3 hours.

10. A process according to claim 9, wherein step (2) is carried out in the presence of a solvent to assist the removal of water.

11. A process according to claim 8, wherein step (1) is carried out by spraying or by means of a screw-rod applicator.

12. A composition of matter according to claim 1, wherein Iso bears at least one other function of the following formula:

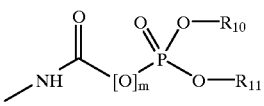

wherein:

m is equal to 0 or 1;

$R_{10}$ is a negative charge or a residue containing hydrogen and carbon atoms whose point of attachment is a carbon atom; and $R_{11}$ is a negative charge or a group of formula II:

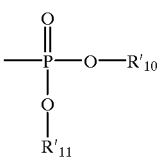

wherein $R'_{10}$ is a residue containing hydrogen and carbon atoms, or a negative charge whose point of attachment is a carbon and wherein $R'_{11}$ is a residue containing hydrogen and carbon atoms whose point of attachment is a carbon atom, or a negative charge.

13. A composition of matter according to claim 1, wherein Iso bears at least two other functions of the following formula:

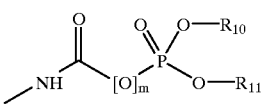

wherein:

m is equal to 0 or 1;

$R_{10}$ is a negative charge or a residue containing hydrogen and carbon atoms whose point of attachment is a carbon atom; and $R_{11}$ is a negative charge or a group of formula II:

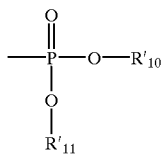

wherein $R'_{10}$ is a residue containing hydrogen and carbon atoms, or a negative charge whose point of attachment is a carbon and wherein $R'_{11}$ is a residue containing hydrogen and carbon atoms whose point of attachment is a carbon atom, or a negative charge.

14. A composition of matter according to claim 1, being an isocyanate, wherein all of the isocyanate functions are converted into functions of the formula:

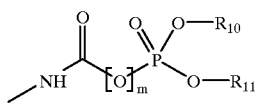

wherein:

m is equal to 0 or 1;

$R_{10}$ is a negative charge or a residue containing hydrogen and carbon atoms whose point of attachment is a carbon atom; and $R_{11}$ is a negative charge or a group of formula II:

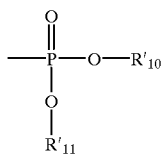

wherein $R'_{10}$ is a residue containing hydrogen and carbon atoms, or a negative charge whose point of attachment is a carbon and wherein $R'_{11}$ is a residue containing hydrogen and carbon atoms whose point of attachment is a carbon atom, or a negative charge.

15. A composition of matter according to claim 1, being an isocyanate, wherein all of the isocyanate functions are converted into functions of the formula:

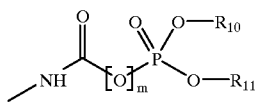

wherein:

m is equal to 0 or 1;

$R_{10}$ is a negative charge or a residue containing hydrogen and carbon atoms whose point of attachment is a carbon atom; and $R_{11}$ is a negative charge or a group of formula II:

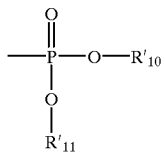

wherein $R'_{10}$ is a residue containing hydrogen and carbon atoms, or a negative charge whose point of attachment is a carbon and wherein $R'_{11}$ is a residue containing hydrogen and carbon atoms whose point of attachment is a carbon atom, or a negative charge; and wherein said isocyanate is di-, tri-, tetra-, penta-, hexa- or heptafunctional with isocyanate function.

16. A composition of matter according to claim 1, wherein said isocyanate is an aliphatic isocyanate.

17. A composition of matter according to claim 1, wherein said isocyanate is a prepolymer of difunctional aliphatic isocyanates.

18. A composition of matter according to claim 17, wherein the prepolymer bears an isocyanurate group, an uretidine dione structure, a biuret, or an allophanate structure.

19. A composition of matter according to claim 18, wherein the prepolymer bears an isocyanurate group and an uretidine dione structure.

20. A composition of matter according to claim 17, wherein the prepolymer is a difunctional isocyanate selected from the group consisting of aliphatic diisocyanates, cycloaliphatic diisocyanates, and arylenedialkylene diisocyanates.

21. A composition of matter according to claim 20, wherein the difunctional isocyanate is a polymethylene diisocyanate or an isophorone diisocyanate.

22. A composition of matter according to claim 21, wherein the difunctional isocyanate is hexamethylene diisocyanate.

23. A composition of matter according to claim 17, wherein said isocyanate comes from biurets and from trimers of polymethylene diisocyanates by replacement of the isocyanate functions with functions of the formula;

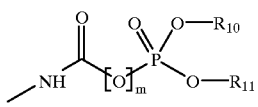

wherein:

m is equal to 0 or 1;

$R_{10}$ is a negative charge or a residue containing hydrogen and carbon atoms whose point of attachment is a carbon atom; and $R_{11}$ is a negative charge or a group of formula II:

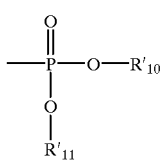

wherein $R'_{10}$ is a residue containing hydrogen and carbon atoms, or a negative charge whose point of attachment is a carbon and wherein $R'_{11}$ is a residue containing hydrogen and carbon atoms whose point of attachment is a carbon atom, or a negative charge.

* * * * *